US010964419B2

(12) United States Patent
Childress et al.

(10) Patent No.: US 10,964,419 B2
(45) Date of Patent: Mar. 30, 2021

(54) INTELLIGENT CONTAINER AND METHOD FOR MEDICINE DISPENSING CONTROL

(71) Applicant: International Business Machines Corporation, Armonk, NY (US)

(72) Inventors: Rhonda L Childress, Austin, TX (US); David Bruce Kumhyr, Austin, TX (US); Michael John Spisak, East Northport, NY (US)

(73) Assignee: International Business Machines Corporation, Armonk, NY (US)

( * ) Notice: Subject to any disclaimer, the term of this patent is extended or adjusted under 35 U.S.C. 154(b) by 509 days.

(21) Appl. No.: 14/886,786

(22) Filed: Oct. 19, 2015

(65) Prior Publication Data

US 2017/0109498 A1   Apr. 20, 2017

(51) Int. Cl.
*G16H 40/67* (2018.01)
*G16H 20/13* (2018.01)

(52) U.S. Cl.
CPC ............ *G16H 20/13* (2018.01); *G16H 40/67* (2018.01)

(58) Field of Classification Search
CPC ............ G06F 19/3462; G06F 19/3418; G06F 19/3456; A61J 7/0427; A61J 2200/30; A61J 7/0418; A61J 1/1412
See application file for complete search history.

(56) References Cited

U.S. PATENT DOCUMENTS

| 8,212,658 | B2 | 7/2012 | Monroe | |
|---|---|---|---|---|
| 8,754,769 | B2 | 6/2014 | Stein | |
| 2005/0191066 | A1* | 9/2005 | Yamazaki | G03G 15/168 399/21 |
| 2014/0262918 | A1 | 9/2014 | Chu | |
| 2014/0347175 | A1 | 11/2014 | Stein | |
| 2015/0278479 | A1* | 10/2015 | Ervin | A61J 7/0418 700/237 |
| 2015/0310185 | A1* | 10/2015 | Shah | G16H 20/10 340/10.6 |
| 2016/0220180 | A1* | 8/2016 | Fateh | A61B 5/4833 |

* cited by examiner

*Primary Examiner* — Reginald R Reyes
(74) *Attorney, Agent, or Firm* — Jeffrey S LaBaw; Richard H Wilhelm; William Stock (57) ABSTRACT

A method for monitoring medicine dispensing is disclosed. A set of events from an intelligent container is received. The intelligent container belongs to a set of intelligent containers, each container associated with a medicine. It is determined whether the set of events satisfies a rule associated with the intelligent container. If the rule is satisfied, a message is created to be sent to a subscribing device as a result of the determination.

20 Claims, 8 Drawing Sheets

INTELLIGENT CONTAINER AND METHOD FOR MEDICINE DISPENSING CONTROL

BACKGROUND

Technical Field

This disclosure relates generally to the field of medicine dispensing, and more particularly to an intelligent container and method for controlling access to medicine and medicine dispensing.

Background of the Related Art

It is estimated that over 100 million people in the United States alone suffer from chronic illness for which medicine is prescribed to cure or ameliorate. Yet patient adherence to the medicine regimen prescribed by medical professionals is poor. Unfortunately, a major reason that patients do not adhere to the medicine regimen is forgetfulness. With aging, patients forget to take their medicine or overdose because they do not remember that they have already taken their medicine. Although many elderly patients have younger relatives, these relatives often do not live with them and so are unable to directly supervise; questioning the elderly patient can lead to inaccurate, evasive or hostile answers as to whether the proper dose of medicine was taken at the appropriate time.

Another problem is those with chronic illness often live in a facility such as an assisted living facility. Tracking the use of medicine, making sure that the correct patients receive the correct drug at the correct time consumes a great deal of the caregivers' time. Some medicines are very expensive and valuable on the black market. Workers at assisted living facilities are not well paid and the situation can lead to a diversion of drugs from the patient.

Tracking the status and location of medicines is of broad importance.

BRIEF SUMMARY

According to this disclosure, a method for monitoring medicine dispensing is disclosed. A set of events from an intelligent container is received. The intelligent container belongs to a set of intelligent containers, each container associated with a medicine. It is determined whether the set of events satisfies a rule associated with the intelligent container. If the rule is satisfied, a message is created to be sent to a subscribing device as a result of the determination.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF AN ILLUSTRATIVE EMBODIMENT

Figure 1:
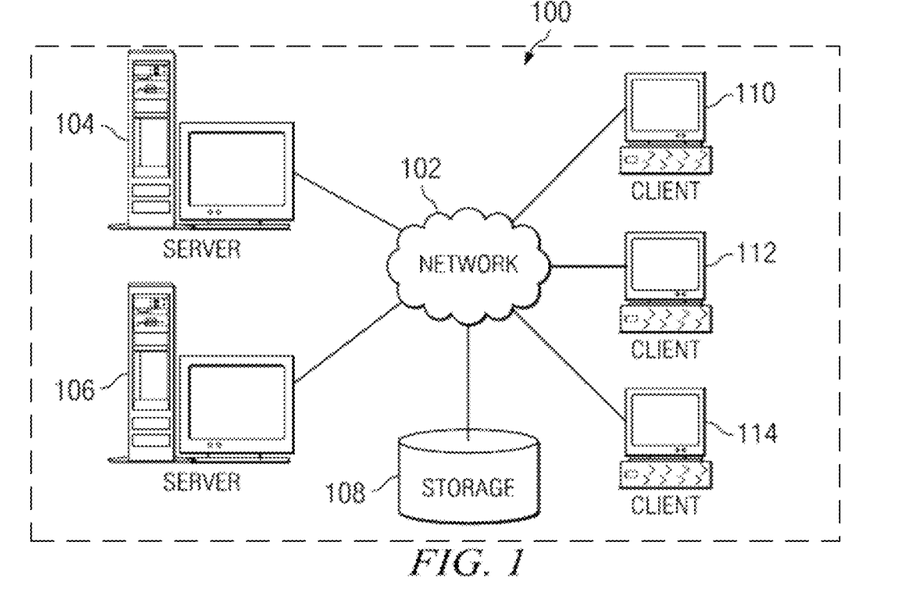
FIG. 1 depicts an exemplary block diagram of a distributed data processing environment in which exemplary aspects of the illustrative embodiments may be implemented.
Figure 2:
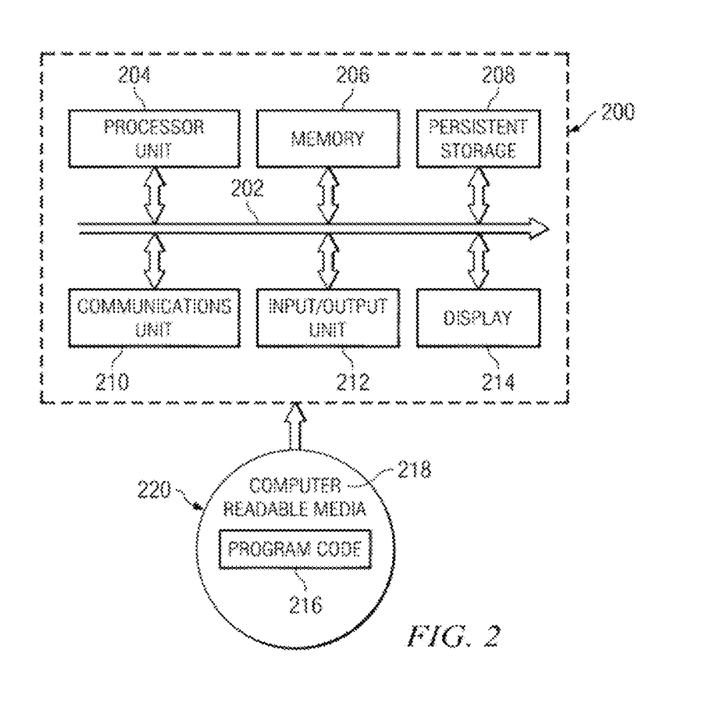
FIG. 2 is an exemplary block diagram of a data processing system in which exemplary aspects of the illustrative embodiments may be implemented.

With reference now to the drawings and in particular with reference to FIGS. 1-2, exemplary diagrams of data processing environments are provided in which illustrative embodiments of the disclosure may be implemented. It should be appreciated that FIGS. 1-2 are only exemplary and are not intended to assert or imply any limitation with regard to the environments in which aspects or embodiments of the disclosed subject matter may be implemented. Many modifications to the depicted environments may be made without departing from the spirit and scope of the present invention.

With reference now to the drawings, FIG. 1 depicts a pictorial representation of an exemplary distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the disclosed subject matter, and therefore, the particular elements shown in FIG. 1 should not be considered limiting with regard to the environments in which the illustrative embodiments of the present invention may be implemented.

With reference now to FIG. 2, a block diagram of an exemplary data processing system is shown in which aspects of the illustrative embodiments may be implemented. Data processing system 200 is an example of a computer, such as client 110 in FIG. 1, in which computer usable code or instructions implementing the processes for illustrative embodiments of the disclosure may be located.

With reference now to FIG. 2, a block diagram of a data processing system is shown in which illustrative embodiments may be implemented. Data processing system 200 is an example of a computer, such as server 104 or client 110 in FIG. 1, in which computer-usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor (SMP) system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer-usable program code, or computer-readable program code that may be read and executed by a processor in processor unit 204. The program code in the different embodiments may be embodied on different physical or tangible computer-readable media, such as memory 206 or persistent storage 208.

Program code 216 is located in a functional form on computer-readable media 218 that is selectively removable and may be loaded onto or transferred to data processing system 200 for execution by processor unit 204. Program code 216 and computer-readable media 218 form computer program product 220 in these examples. In one example, computer-readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer-readable media 218 also may take the form of a persistent storage, such as a hard drive, a thumb drive, or a flash memory that is connected to data processing system 200. The tangible form of computer-readable media 218 is also referred to as computer-recordable storage media. In some instances, computer-recordable media 218 may not be removable.

Alternatively, program code 216 may be transferred to data processing system 200 from computer-readable media 218 through a communications link to communications unit 210 and/or through a connection to input/output unit 212. The communications link and/or the connection may be physical or wireless in the illustrative examples. The computer-readable media also may take the form of non-tangible media, such as communications links or wireless transmissions containing the program code. The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown. As one example, a storage device in data processing system 200 is any hardware apparatus that may store data. Memory 206, persistent storage 208, and computer-readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

Computer program code for carrying out operations of the present invention may be written in any combination of one or more programming languages, including an object-oriented programming language such as Java™, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Those of ordinary skill in the art will appreciate that the hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system, other than the SMP system mentioned previously, without departing from the spirit and scope of the disclosed subject matter.

As will be seen, the techniques described herein may operate in conjunction within the standard client-server paradigm such as illustrated in FIG. 1 in which client machines communicate with an Internet-accessible Web-based portal executing on a set of one or more machines. End users operate Internet-connectable devices (e.g., desktop computers, notebook computers, Internet-enabled mobile devices, or the like) that are capable of accessing and interacting with the portal. Typically, each client or server machine is a data processing system such as illustrated in FIG. 2 comprising hardware and software, and these entities communicate with one another over a network, such as the Internet, an intranet, an extranet, a private network, or any other communications medium or link. A data processing system typically includes one or more processors, an operating system, one or more applications, and one or more utilities. The applications on the data processing system provide native support for Web services including, without limitation, support for HTTP, SOAP, XML, WSDL, UDDI, and WSFL, among others. Information regarding SOAP, WSDL, UDDI and WSFL is available from the World Wide Web Consortium (W3C), which is responsible for developing and maintaining these standards; further information regarding HTTP and XML is available from Internet Engineering Task Force (IETF). Familiarity with these standards is presumed.

Figure 3:
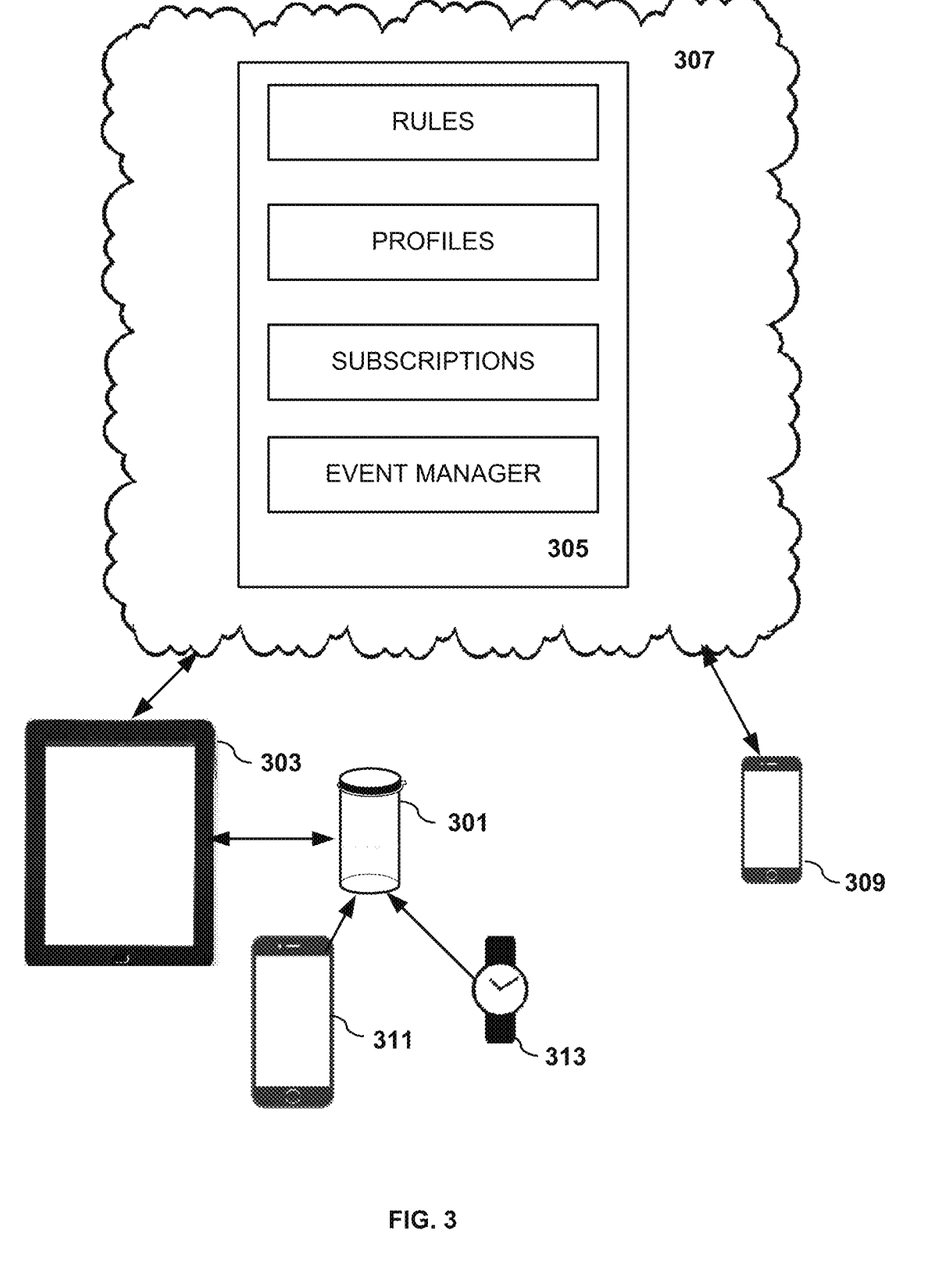
FIG. 3 is a representative medicine management system in which the disclosed subject matter may be implemented.

FIG. 3 shows one illustrative environment in which a preferred embodiment of the invention can be used. One intelligent container 301 of a set of intelligent containers is shown wirelessly coupled to tablet 303. In other embodiments of the invention, a wired connection such as a USB cable is used during certain processes of the embodiment such as container configuration. During system configuration, it is useful to have a display and input device to register a new medicine into the system. A tablet computer running a client version of the medicine dispensing application is useful to provide these capabilities, however, in alternative embodiments other computing devices such as laptop computers and smart phones, or special purpose devices can be used. Although only a single intelligent container is shown for clarity, in most embodiments of the invention, multiple containers would be controlled by the system. However, some embodiments of the invention have a single intelligent container in the set of intelligent containers.

The tablet computer 303 communicates to a server computer 305, similar to those described above in association with FIGS. 1 and 2. Preferably, the server 305 is resident in a cloud environment 307 or is a web server. The medicine dispensing server application 305 receives information from the tablet computer 303 during the registration process so that the medicine which has been placed in the intelligent container can be monitored and disseminated to subscribing devices such as smart phone 309. In other embodiments of the invention, multiple subscribing devices can receive events from the server application.

As will be described in greater detail below, the intelligent container 301 has wireless communication capabilities using protocols such as NFC, WiFi, Bluetooth, RFID or other short range protocols. Some preferred embodiments use a combination of protocols so that they are compatible with a greater variety of devices. Thus, the intelligent container can sense neighboring devices such as smart phone 311 and smart watch 313, even if the neighboring devices do not have a client version of the medicine dispensing application resident. This sensed information can contain device ID data such as an IMEI number from a smart phone which can help identify neighboring devices which are proximate to the intelligent container 301 when an event or set of events is sensed, such as a move event, a cap off event or a tilt event. The device ID data can be useful for identifying the party responsible for the sensed event. Other sensed events can include location events from an embedded or proximate accelerometer, GPS or cell phone tower, movement events in x, y and z axes, g forces, pressure, and temperature changes. A single event can be in the set of events transmitted to the server 305. For the purposes of this invention, an event generally falls into the category of a sensor detection event or the category of an ID sensed event. Often a sensor detection event will be in the same set of events or concurrently sensed as an ID sensed event.

Further, the intelligent container 301 can use capabilities from neighboring devices as part of the registration process or monitoring process. For example, a bar code reader or QR code reader application or OCR application on the tablet could be used to capture medicine data for a new medicine bottle to be inserted into the intelligent container 301 during the registration process. Using such a reader can greatly speed the entry of data during registration, as well as provide a means of securely entering encoded information via the bar code or QR code, i.e. guaranteeing the accuracy of the entered information. During the monitoring process, GPS data or cell tower location data from a neighboring device can be used to monitor the location of the intelligent container, without requiring the container itself to possess the locator capability.

In the application 305, rules are used by the event manager to determine whether an event at the intelligent container 301 occurred. Preferably, the rules are in a rule store so that new rules can be easily added to the application, although in other embodiments of the invention the rules are hardcoded to prevent tampering. A user profile is used to contain information about a particular user having medicine controlled by the medicine dispensing application. A container profile is used to contain information about the medicine contained within a particular intelligent container, e.g., dosage(s), time(s) that the medicine should be taken, patient name(s). A user profile will typically be associated with one or more intelligent container profiles. In certain health care settings, a particular intelligent container profile can be associated with multiple user profiles, if multiple patients are given the same drug.

Figure 4A:
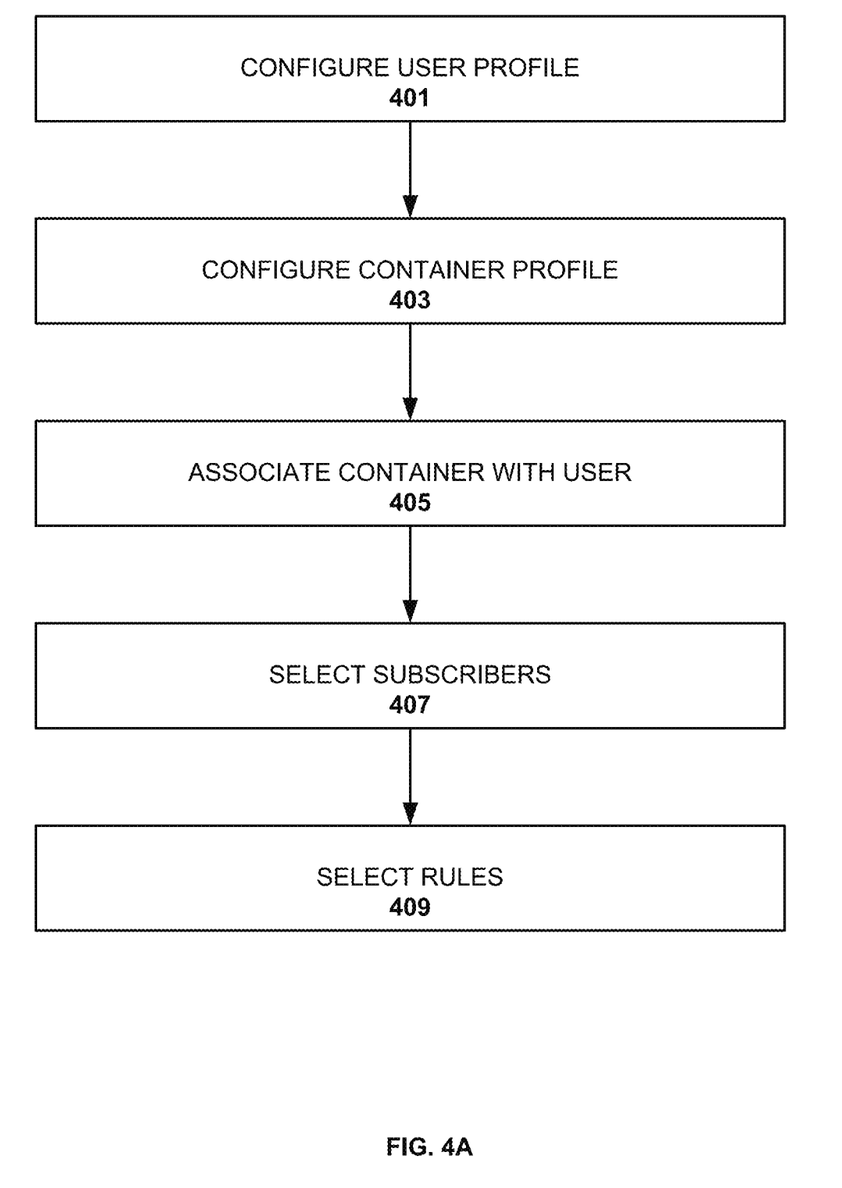
FIG. 4A is a flow diagram for system configuration of the medicine management system.

One embodiment for a system configuration process of entering a new medicine into the medicine management system is shown generally in FIG. 4A. The flow diagram begins in step 401 where the user profile for a new or existing user is configured for the addition of the new medicine. In the case of an existing user, the new drug information is associated with the user in steps below. In the case of a new user, user information data such as name, age, address or room number, doctor(s) are entered. In some preferred embodiments of the invention, part of a profile contains user preferences in connection with taking medicines such as a preferred time to take medicine, whether large pills should be cut for easier swallowing, which medicines need to be taken with food and so forth. Part of the user profile preferably includes a record of the medicines assigned to the user, dates that the prescriptions were filled and refilled, and so forth.

In step 403, the container profile is configured. The intelligent container of the present invention is shaped so that a standard sized prescription bottle can be inserted into a top sleeve of the container. Once the prescription has been consumed or otherwise emptied, the intelligent container can be reused to house a different medicine. Therefore, there needs to be a new association of the particular intelligent container with the new medicine or medicine refill. Medicine information will include the name of the medicine, both trade name and generic name, the dosage, times per day that the medicine is to be taken as well as other instructions for taking the medicine. As is mentioned above, in some embodiments of the invention, the medicine data can be entered by means of a bar code reader, a QR code reader or OCR. In some embodiments of the invention, configuration or registration of a new container profile is triggered responsive to detecting a new medicine bottle has been inserted into the intelligent container.

Step 405 associates the container profile for the new medicine with the user profile. During the association process, a view of the other medicines and corresponding intelligent containers previously associated with the user profile can be presented to the user. In preferred embodiments of the invention, an automatic check is made for drug interactions with previously entered medicines that have been entered into the system that the user is taking. This view can show redundant medicines as well as a current level of medicine in the intelligent container, so as to alert the user when reordering the prescription is needed. In the preferred embodiment of the invention, the current level of medicine is calculated by the dosage instructions in combination with the number of cap off and tilt events detected as discussed in greater detail below. Rather than counting pills, in the preferred embodiment, the combination of a cap off and tilt event at a scheduled time is assumed to increment the number of pills in the bottle by the dosage amount.

The subscribers to the events detected by the intelligent container can be selected in step 407. In one preferred embodiment, a subscriber will receive all of the events associated with a particular user profile. For example, a relative may be concerned that an elderly individual is taking their medicines accurately. So they will want to know about all of the medicines taken to help monitor how the individual is complying with their medicine regimen. In another preferred embodiment, a subscriber may only be concerned with a single medicine or class of medicines. For example, a doctor may only be concerned with a single medicine which she prescribed, and so would be a subscriber to only the events associated with a single container. Thus, if the medicine regimen was not being followed, or in response to a patient complaint, the doctor could remind the patient to take their medicine at the prescribed schedule. As another example, a health facility may be concerned with controlling a class of addictive or expensive medicines, so a hospital administrator may be a subscriber to events from any intelligent container whose profile indicates it is associated with a narcotic. Generally, a subscriber to an event will receive the event once is has been collected and logged by the medicine dispensing system server. In the case of subscribing applications which are not constantly logged on to the server, the subscriber will receive all of the events from a last logon or other contact with the server.

In this step, the type of notification can be selected. For a relative who wants to be generally aware of an elderly individual's medicine regime, it may be adequate to receive an update and recent history when they open up the medicine dispensing app on their smart phone. On the other hand, events which indicate that a narcotic is being stolen may warrant an alert event, such as an SMS text, to a hospital administrator smart phone. Some examples of such events (or combinations of events) are as follows, a cap off event which does not conform to a patient schedule, a removal event when the status of the intelligent container indicates that the medicine bottle still contains narcotics or location events which indicate an unauthorized individual is moving one or more intelligent containers to an unauthorized location.

The subscribers to events receive the events by means of a client application on a subscribing device, e.g., the medicine dispensing application in the tablet 303 or the application in the subscribing smart phone 309. These events are typically received outside the configuration process in preferred embodiments of the invention.

In step 409, rules are configured for the container profile and/or user profile. These rules typically include patient, dose, time of day and location information. They may also include a list of authorized users and caregivers. The rules contained in a user profile could overrule those entered initially in a container profile for ease in administering medication to a patient. For example, with a user profile already associated with a number of container profiles, a message could be presented to the user configuring the new medication: "You entered that the medicine must be administered at 4 PM. Other medicines are being administered at 5 PM. Can this time be changed to 5 PM?" In general, the system will expect tilt and cap off events to correspond to the scheduled times of administering the invention. Certain windows of time can be specified within which a rule can be considered to be satisfied, e.g., if a medicine is taken in a one hour window around a specified time the rule is considered satisfied. A rule can be considered to be "associated" with an intelligent container if it is a container rule, a user profile rule belonging to a user associated with the intelligent container or a medicine rule for the medicine in the intelligent container.

These rules can be used to determine an out of schedule event, indicating a possible problem, e.g., pilferage, overdose or noncompliance with medicine regimen. For example, a tilt and cap off event with IMEI data from an unauthorized user could indicate pilferage of a controlled substance. Multiple tilt and cap off events with IMEI data from an authorized user could indicate an overdose situation. The lack of expected tilt and cap off events at expected times can indicate a lack of compliance with a medicine regimen.

Figure 4B:
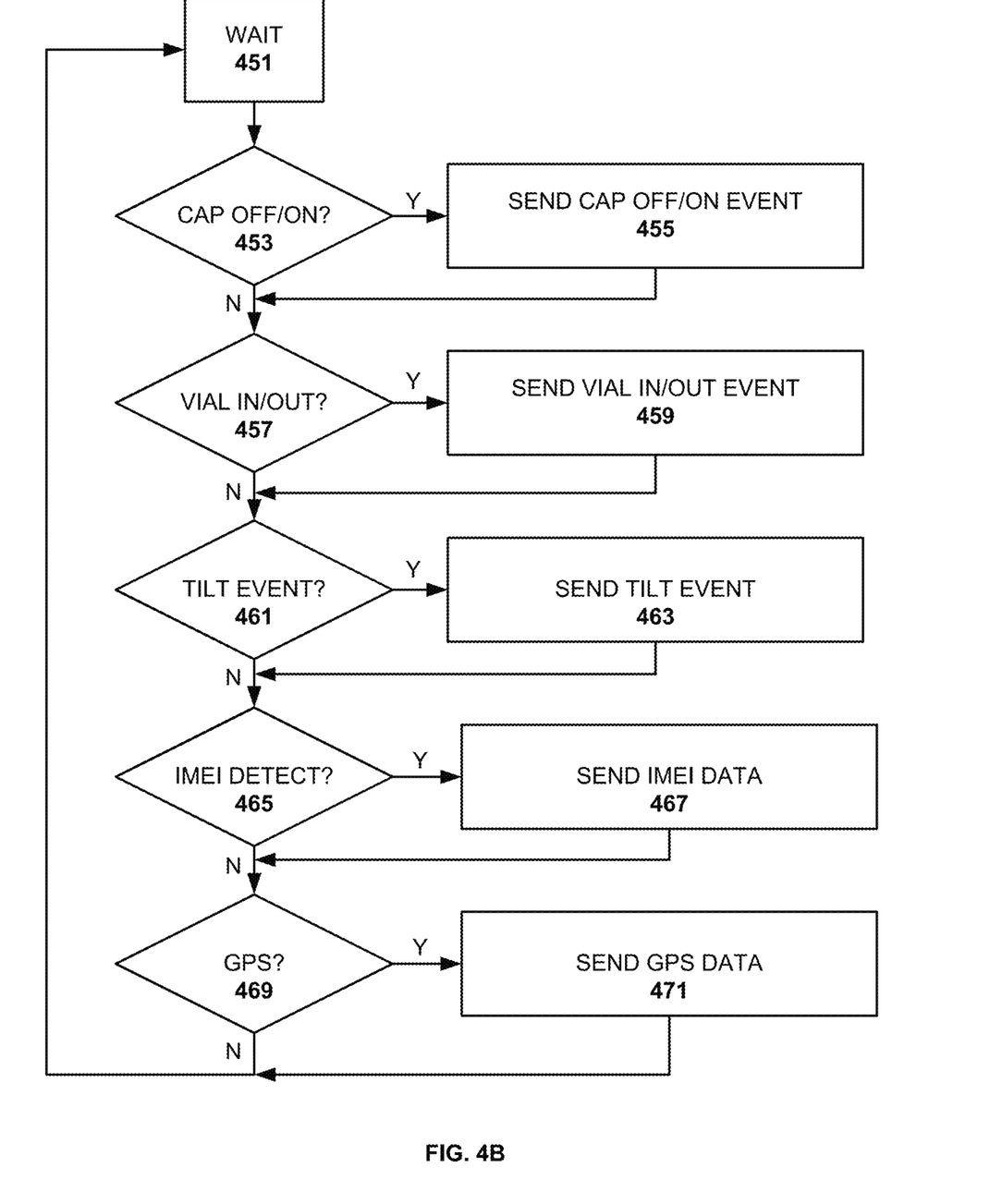
FIG. 4B is a flow diagram for event detection by the intelligent container.

FIG. 4B is a flow diagram for event detection by the intelligent container. As will be discussed below in greater detail, the intelligent container comprises a number of sensors, a processor and memory for storing application instructions and a wireless connection for communicating sensed events to the medicine dispensing system. The drawing illustrates one preferred embodiment of the invention. The process begins in step 451 where the process is in a wait mode. Next, in step 453, a test is conducted to determine whether a cap off or cap on event has been sensed by the cap sensor. If so, in step 455, a cap of or cap on event is sent wirelessly to the medicine dispensing system. If not, the process continues to step 457. Next, in step 457, a test is conducted to determine whether a vial in or out event has been sensed by the pressure sensor. If so, in step 459, a vial in or vial out event is sent wirelessly to the medicine dispensing system. If not, the process continues to step 461.

A test is conducted in step 461 to determine whether a tilt event has been sensed by the tilt sensor or accelerometer. If so, in step 463, a tilt event is sent wirelessly to the medicine dispensing system. If not, the process continues to step 465. Next, in step 465, a test is conducted to determine whether an IMEI or other device signature has been detected from a nearby wireless device. If so, in step 467, the collected device signature data is sent wirelessly to the medicine dispensing system. If not, the process continues to step 469. Location date is collected in step 469, either from onboard sensors, or from nearby devices with sensors for such information. If such data has been collected, in step 471, the location data is sent wirelessly to the medicine dispensing system. Next, the process continues to step 451 wherein the processor waits for new events.

Figure 5:
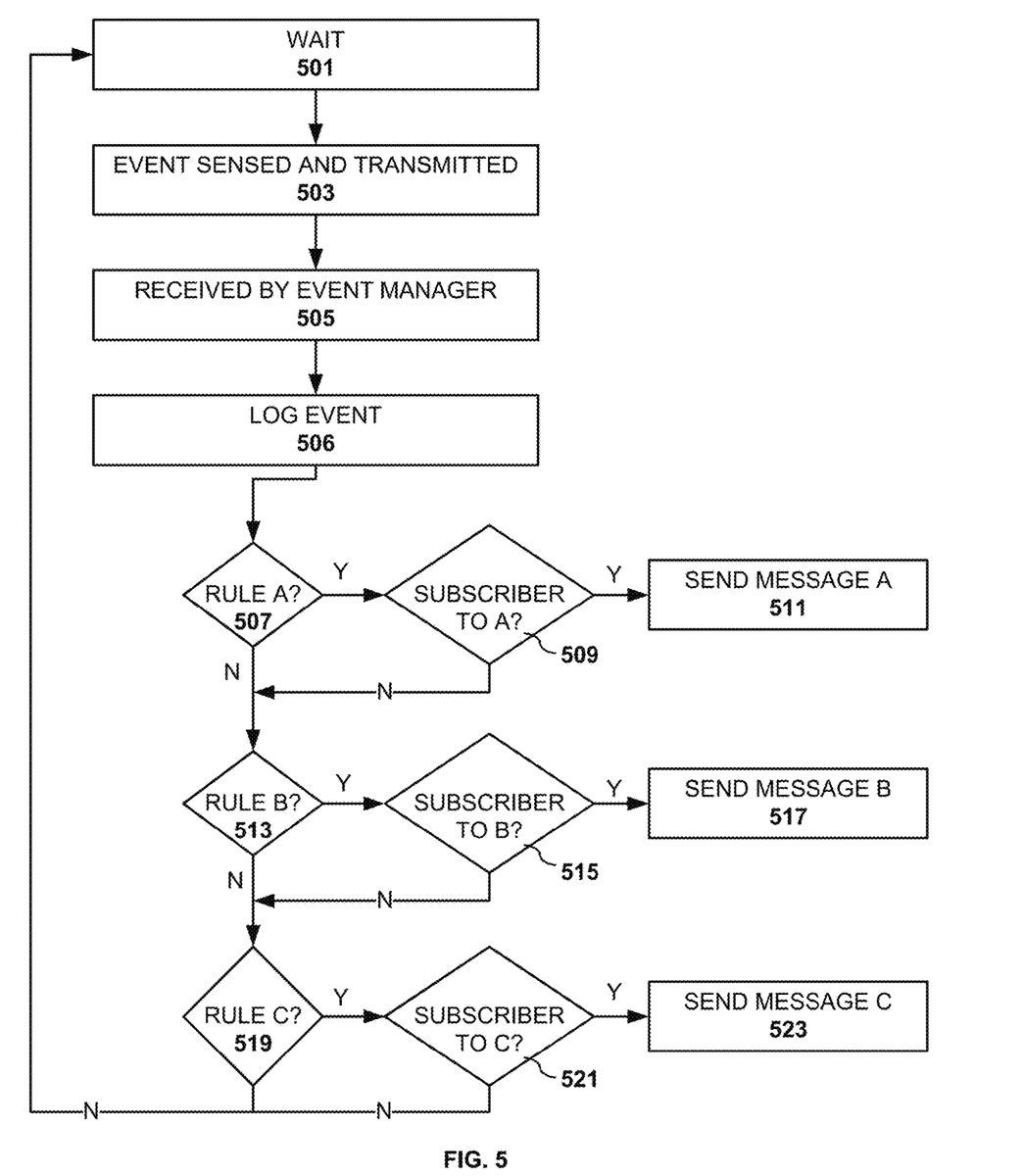
FIG. 5 depicts a process flow of the event handling by the event manager of the invention.

FIG. 5 depicts a process flow of the event handling by the event manager of the invention. In step 501, the system waits for events to be sensed by one or more intelligent containers. In step 503, a container event such as a cap on, cap off or tilt event is sensed and transmitted to the medicine dispensing server application in a cloud environment or web server. The event manager receives the event, step 505. The event is logged for later use by the event manager or subscribers.

Next, a set of tests is used to determine whether the detected events match respective rules within the set of rules to qualify for transmission to a subscriber. Only three generalized rules are shown for ease in illustration, but those skilled in the art would recognize that there can be as many rules as can be supported by the capabilities of the system. Some of the rules or policies typically comprise combinations of events and data that signify authorized, unauthorized and suspicious activities. Obviously, the detection of unauthorized or suspicious activity would warrant investigation which can be accomplished at least in part by an examination of the event log. In step 507, a test is made whether the detected event matches Rule A. Rule A, for example, could be a cap off event for medicine A at a time of 5 PM within an hour time window. This is an example of an authorized activity. If the event satisfies the test, it is sent to step 509 to determine whether there are any subscribers to a Rule A event. If so, an appropriate message is transmitted to the subscribers of Rule A in step 511. Subscribers of a rule could include interested relatives, doctors and other health care professionals as well as administrators tasked with controlling the dispensing of controlled substances.

In step 513, a test is made whether the detected event(s) matches Rule B. For example, Rule B could be a tilt event for medicine A at any time. If the event satisfies the test, it is sent to step 515 to determine whether there are any subscribers to a Rule B event. If so, an appropriate message is transmitted to the subscribers of Rule B in step 517.

In step 519, a test is made whether the detected event(s) matches Rule C. Rule C is an example of a rule which requires more than one event to satisfy. For example, the rule could be a combination of a cap off event and tilt event for medicine B at a time of 5 PM within an hour time window and at a specified location by an authorized user. To determine whether the rule is satisfied may require that the application review the event log to see if the requisite events have already been detected and logged. If the logged events satisfy the test, step 521 determines whether there are any subscribers to a Rule C event. If so, an appropriate message is transmitted to the subscribers of Rule C in step 523.

In other embodiments of the invention, messages can be sent to subscribers in the event of violations of rules. Using the above example, if a cap off and tilt event for medicine B occurred at a specified location, but it was neither within the hour time window nor by an authorized user, a message could be sent to a subscriber who subscribed to a rule violation stream. This is an example of an unauthorized activity. In yet other embodiments, a rule could be created explicitly for the purpose of alerting a user to unauthorized activity. In these embodiments, a rule could be created "if an event is detected outside an authorized time window, alert the subscribing users" or "if an event is detected outside an authorized set of locations, alert the subscribing users".

Figure 6:
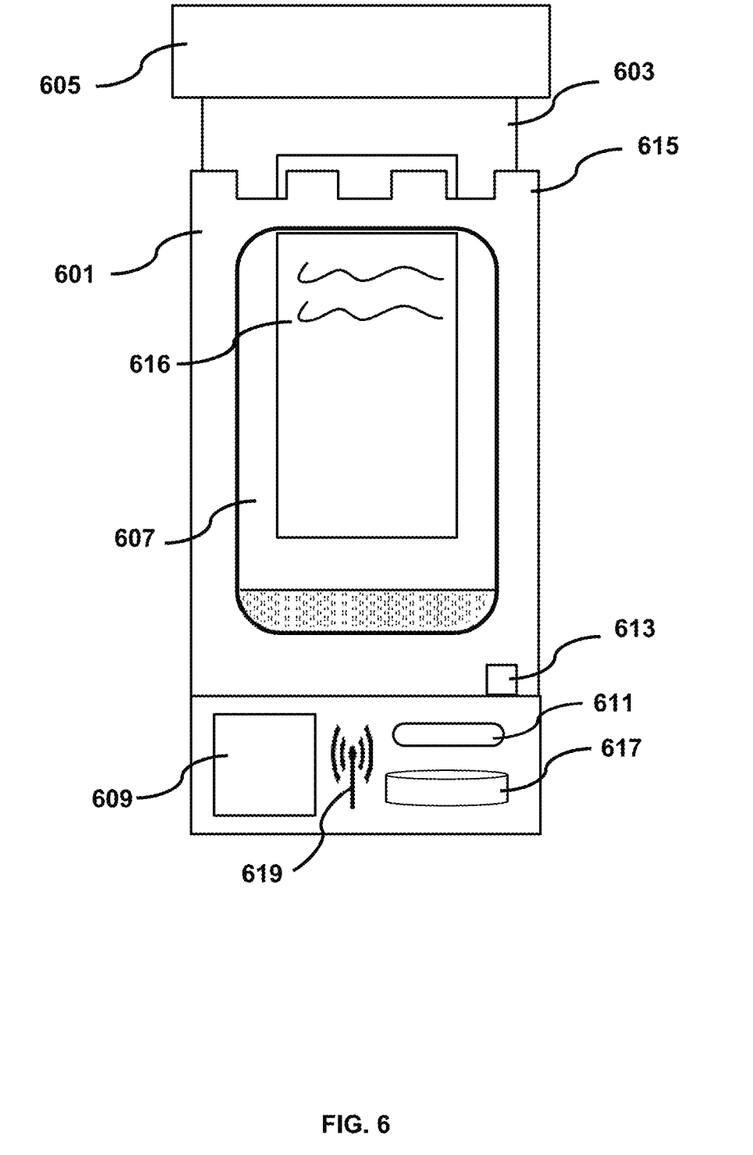
FIG. 6 shows one embodiment of the intelligent container.

FIG. 6 shows one embodiment of the intelligent container. The container body 601 is shaped so a standard medicine bottle 603 and cap 605 be inserted and locked in place in a sleeve like opening. A window 607 is provided so that the label can be read without removing the medicine bottle 603. Since reuse of the intelligent container is envisioned, preferably it is composed of a sturdy material such as metal or plastic which is compatible with the circuitry contained therein. Processor and memory 609 are housed in a bottom electronics compartment of the container together with an accelerometer 611 or other tilt detecting device to detect a tilt event. Other embodiments of the invention could locate the electronics compartment in the sidewall or other portion of the intelligent container. Pressure sensor 613 detects that a medicine bottle is inserted or is removed. It can be used as a signal that registration of a new medicine should begin, or an unauthorized removal of a registered medicine. The cap sensor 615 is used to sense a cap on or cap off event. Notches 611 engage the standard tabs at the lip of the bottle to prevent rotation of the bottle 603 when the cap 603 is turned. Battery 617 powers the electronics as well as providing power to the antenna 619 for wireless communications. The processing requirements for the processor are relatively modest, in commercial versions of the intelligent container a custom chip is likely. Prototypes have used the Broadcom Wiced Sense as the processor. The pressure sensor 613 and cap sensor 615 can be a pressure sensing device, or a capacitance or optical sensor could be used to sense the medicine bottle in/out and cap on/off events.

The inventors recognize that there are a range of "standard-sized" medicine bottles. Thus, in some embodiments of the invention, there are a range of sizes in the set of intelligent containers used in the medicine dispensing system, e.g., a set of intelligent containers sized to house 6, 8, 13, 20, 30, 40, 60 dram bottles. An arrangement with a pharmacy could be established a prior to furnish medicine bottles in a subset of the available standard bottles. O-ring shaped spacers are provided in alternative embodiments of the invention so that one size of intelligent containers can be used to house more than one size of "standard-sized" bottles.

Figure 7A:
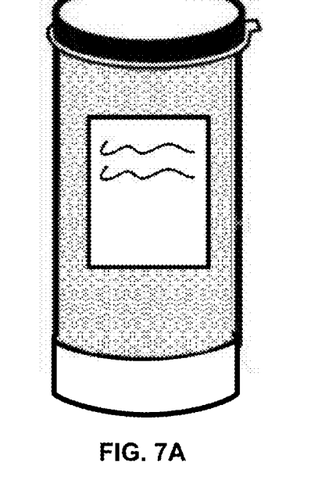
FIGS. 7A and 7B show an embodiment of the invention in which the medicine bottle can be twisted into a privacy mode.
Figure 7B:
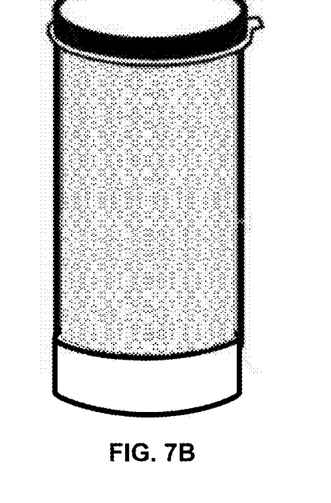

FIGS. 7A and 7B show an embodiment of the invention in which the medicine bottle can be twisted into a privacy mode. In FIG. 7A, the medicine bottle is in a first position in which the medicine label can be read. This is useful for reading the label information and ascertaining that the correct medicine is being taken. However, some users may not want others to know the drugs that they are taking. Therefore, in some embodiments of the invention, a privacy mode can be used in which the medicine bottle is twisted to hide the medicine label as shown in FIG. 7B. Alternatively, a cover can be included in the intelligent container to cover the label area. In the event that privacy was desired, yet a plurality of medicines needed to be tracked an assortment of colors of the containers could be used to differentiate one medicine from another.

Figure 7C:
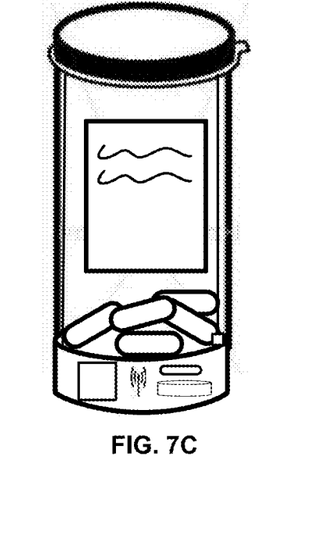
FIG. 7C shows an embodiment of the invention in which a transparent material is used so that a condition of the medicine bottle and medicine can be observed.

FIG. 7C shows an alternative embodiment of the invention in which a transparent material is used so that a condition of the medicine bottle and medicine can be observed without removing the medicine bottle from the intelligent container, and therefore triggering an event. This embodiment is useful in an institutional setting and when a nurse or other health worker is monitoring whether a refill order may be required from the pharmacy, or a hospital administrator is investigating unexplained, out of schedule events. Electrical connections to the cap sensor can be made of a transparent conductor if desired for aesthetic reasons.

Figure 8A:
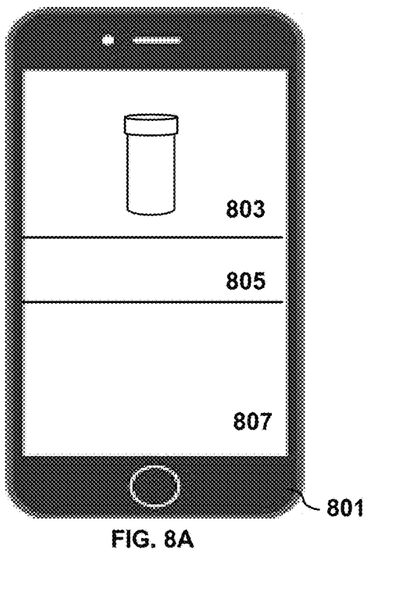
FIGS. 8A-8C show a representative display interface that may be used to display events according to this disclosure.
Figure 8B:
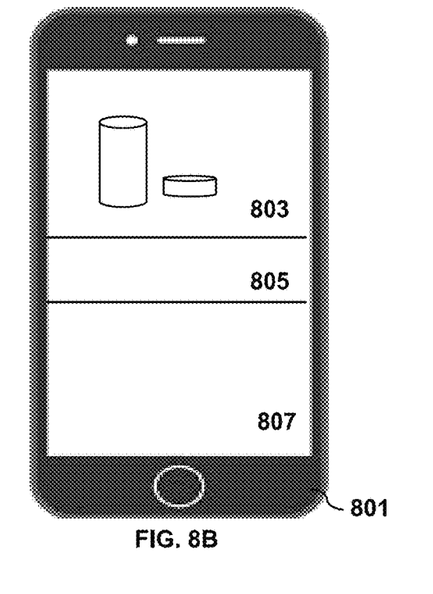
Figure 8C:
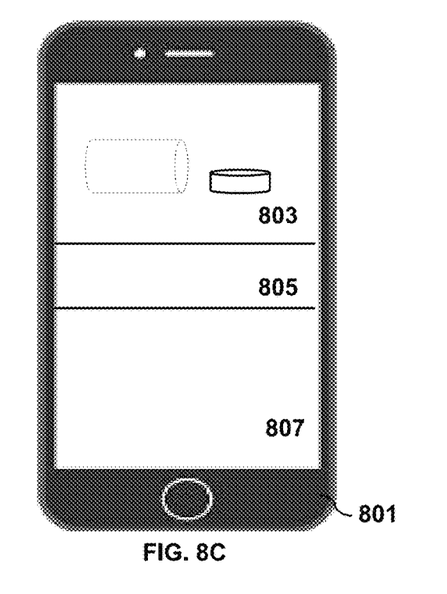

FIGS. 8A-8C show a representative display interface that may be used to display events according to this disclosure. As shown in the drawings, a subscriber is updated on the state and events of a particular intelligent container in a user interface displayed on a smart phone 801. Icon area 803 displays a current state of the container by means of an icon or other pictorial information. The icon can be presented in an upright cap on state as shown in FIG. 8A, a cap off state as shown in FIG. 8B or a tilted state as shown in FIG. 8C. Other representations are used in other embodiments of the invention. For example, a cap on state can be generalized as a non-dispensing state and a cap off state can be generalized as a dispensing state. A tilted state can be generalized as a movement state. Alert area 805 is used to display messages which the user has subscribed to indicating whether the current state of the container is in compliance with or has triggered a given rule. History area 807 can be scrollable and displays a set of past events associated with the intelligent container. The log of past events can be used to determine if the user has a history of being in compliance or out of compliance with his medicine regime.

Either the alert area 805 or the history area 807 can be used to display summarized event data or raw event data. For example, in one preferred embodiment, the alert area 805 would display a message stating that a "dispensing" event or a "transport" event has occurred. If the user wants more information, he can drill down on the event and get the raw event data in the history area 807.

In a preferred embodiment, the events are classified into Dispensing, Transport or Replacing events:

Dispensing event: lifting (sensed by accelerometer), top removal (sensed by cap sensor), tilting past 90 degrees (sensed by accelerometer) Transport event: lifting, movement (sensed by accelerometer or GPS)

Replacing event: removing the pill bottle from the sleeve (sensed by pressure sensor), replacing pill bottle (sensed by pressure sensor)

The replacing event triggers the need to register the medication information (prescription number, pill type, dosing information, patient name, identification) with the intelligent container and medicine dispensing service. Any of the above events can trigger a scan and logging of local NFC devices for identification of an authorized or unauthorized user who may be performing actions which trigger the events.

The following are examples of sets of events which are likely to be ones which follow a rule for an authorized activity:

Dispensing event: near a patient, by a person authorized to dispense and in an area where dispensing would likely take place; patient's room, common room, treatments room.

Transport events: from a patients' room or a medication storage area to a dispensing area or along with a patient when being transported.

Replacement events: near a patient, by a person authorized to dispense and in an area where replenishing a medication would likely take place; patient's room, pharmacy.

The following are examples of sets of events which are like to be ones which follow a rule for an unauthorized activity.

Dispensing event: near a closet, outside a side entrance, or other unauthorized area.

Transport events: from a patient's room or a medication storage area to an unauthorized area.

Replacement events: near a closet, outside a side entrance or other unauthorized area.

Two examples of events which might be captured in an embodiment of the invention. In the first, there is a combinations of events that indicate authorized medication dispensing.

First situation: Nurse Ratched, with her employee badge, enters patient Mr. McMurphy's room to dispense pain medication on the recommended dosage schedule at 22:30. She opens and tilts the pill bottle which is enclosed in the intelligent container to retrieve the pills and administer them to Mr. McMurphy.

The intelligent container generates or captures and sends the following events:

Event: Cap off (Opened)
Event: Tilted past 90°
Time: 2015-10-01T22:34:44
GPS: 19.3858738
GPS: −99.1612232
Bluetooth: AYE-AS4-J4G-B4Y
P-RFID: P8973-M81
E-RFID: E0023-2014
Bluetooth: Charge HR 0236
WiFi: TC8717TA6
MEID: A0123456789012

In the set of events above, are the Bluetooth IDs of Nurse Ratched's headset, her fitness watch and her cell phone. Also captured is the RFID data from Mr. McMurphy's wristband and Nurse Ratched's employee ID badge along with the location and time.

In the second situation, there are combinations of events that indicate unauthorized medication dispensing. Second situation: Brandon 'Badger' Mayhew, a night patient attendant at the nursing home, enters patient Mr. McMurphy's room and finds the pill bottle with an OxyContin pain medication. He removes the bottle from the room and goes to a nearby closet. There he opens the bottle and removes the OxyContin pills and replaces them with plain aspirin tablets. Then, he returns the bottle to the room.

The intelligent container generates or captures and sends the following events as Mayhew travels to the closet:

Event: Moving
Time: 2015-10-01T03:12:13
GPS: 19.3858738
GPS: −99.1612232
Bluetooth:
P-RFID: P8973-M81

E-RFID: E0123-2015
Bluetooth:
WiFi:
MEID: C004FH1200000

The intelligent container generates or captures and sends the following events once Mayhew is in the closet and exchanging contents:

Event: Opened
Event: Tilted past 90°
Time: 2015-10-01T03:14:01
GPS: 19.3858940
GPS: −99.1612100
Bluetooth:
P-RFID:
E-RFID: E0123-2015
Bluetooth:
WiFi:
MEID: C004FH1200000

The intelligent container generates or captures and sends the following events as Mayhew returns to the patient room:

Event: Moving
Time: 2015-10-01T03:12:13
GPS: 19.3858738
GPS: −99.1612232
Bluetooth:
P-RFID: P8973-M81
E-RFID: E0123-2015
Bluetooth:
WiFi:
MEID: C004FH1200000

In the first set of events, initially near Mr. McMurphy, is the RFID data from Mr. McMurphy's wristband along with signatures of Badger's cell phone and employee badge. Then as intelligent container is moved away from the room and opened in the closet only Badger's signatures appear in the second set of events. Finally, in the third set of events, the RFID data from Mr. McMurphy's wristband appears as the container is replaced back in Mr. McMurphy's room.

In yet another embodiment of the invention, the intelligent container can include a temperature sensor. This embodiment is useful for medicines which are temperature sensitive like insulin, although adding a temperature sensor could be useful for any medicine kept in an outdoor environment such as camping, military or third world country applications.

In the case diabetes, the design of the sleeve, if not the entire intelligent container, would be smaller to fit an injectable bottle like a Lantus insulin vial. The one danger with insulin is over medicating which is dangerous with insulin. When a patient is elderly with poor memory and attended by more than one caregiver, there is a danger of overdose, e.g., a first caregiver may give the insulin to the patient, and the patient does not recall that the first caregiver has already given the insulin when asked by a second caregiver and a repeat dose is given. The same situation can occur with a pet which is unable to tell caregivers what the other may have done.

An embodiment of the invention can help avoid this problem. A rule can be set up to detect of a multiple dose, within a specified period of time by using the event log. Taking the example of a diabetic cat, the cat gets insulin twice a day, once when fed in the morning and once when fed in the evening. The event log shows the first spouse taking the insulin drawing a dose to administer to the cat at 6:11 when the first spouse leaves for work.

Event: Moving
Event: Tilted past 90°
Time: 2015-10-01T06:11:31
GPS: 19.3858940
GPS: −99.1612100
RFID: PETWATCH 12345
Bluetooth: Fitbit Surge 7199
WiFi: Homebase
MEID: C004FH1200000

The second spouse taking the insulin drawing a dose to administer to the cat at 8:30 assuming the first spouse did not feed and dose the cat.

Event: Moving
Event: Tilted past 90°
Time: 2015-10-01T08:31:11
GPS: 19.3858940
GPS: −99.1612100
RFID: PETWATCH 12345
Bluetooth: Charge HR 0236
WiFi: Homebase In this embodiment, a rule has been set up to alert either spouse that the other has administered a dose to the pet. An alert, for example an SMS message or a notification on the medicine dispensing app in a smart phone indicating "Alert: MULTIPLE DOSE-OVERDOSE POTENTIAL" could be sent to one or both spouses' smart phone(s) to potentially avert the possible overdose. Either spouse knowing that the alert rule has been set up, can wait for a time period after tilting the intelligent container containing the vial to receive the alert. Another alternative would be for the second spouse to review the events recorded for the intelligent container (for example, using the interface discussed above in connection with FIGS. 8A-8C) to see that the first spouse has already administered the medicine.

The subject matter described herein has significant advantages over the prior art. The registration process facilitates the administration of medicine to patients in a home or medical setting. Patients can be monitored for proper adherence to a medical regimen. Also, unexpected events which can indicate diversion of medicine to unauthorized individuals by means of a set of alerts. Caregivers or other authorized individuals can be monitored for following the patient schedules, and if variances are detected, appropriate actions can be taken.

The functionality described above may be implemented as a standalone approach, e.g., a software-based function executed by a processor, or it may be available as a managed service (including as a web service via a SOAP/XML interface). The particular hardware and software implementation details described herein are merely for illustrative purposes are not meant to limit the scope of the described subject matter.

More generally, computing devices within the context of the disclosed subject matter are each a data processing system (such as shown in FIG. 2) comprising hardware and software, and these entities communicate with one another over a network, such as the Internet, an intranet, an extranet, a private network, or any other communications medium or link. The applications on the data processing system provide native support for Web and other known services and protocols including, without limitation, support for HTTP, FTP, SMTP, SOAP, XML, WSDL, UDDI, and WSFL, among others. Information regarding SOAP, WSDL, UDDI and WSFL is available from the World Wide Web Consortium (W3C), which is responsible for developing and maintaining these standards; further information regarding HTTP, FTP, SMTP and XML is available from Internet Engineering Task Force (IETF).

The scheme described herein may be implemented in or in conjunction with various server-side architectures including simple n-tier architectures, web portals, federated systems, and the like. The techniques herein may be practiced in a loosely-coupled server (including a "cloud"-based) environment.

Still more generally, the subject matter described herein can take the form of an entirely hardware embodiment, an entirely software embodiment or an embodiment containing both hardware and software elements. In a preferred embodiment, the function is implemented in software, which includes but is not limited to firmware, resident software, microcode, and the like. Furthermore, as noted above, the identity context-based access control functionality can take the form of a computer program product accessible from a computer-usable or computer-readable medium providing program code for use by or in connection with a computer or any instruction execution system. For the purposes of this description, a computer-usable or computer readable medium can be any apparatus that can contain or store the program for use by or in connection with the instruction execution system, apparatus, or device. The medium can be an electronic, magnetic, optical, electromagnetic, infrared, or a semiconductor system (or apparatus or device). Examples of a computer-readable medium include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. The computer-readable medium is a tangible item.

The computer program product may be a product having program instructions (or program code) to implement one or more of the described functions. Those instructions or code may be stored in a computer readable storage medium in a data processing system after being downloaded over a network from a remote data processing system. Or, those instructions or code may be stored in a computer readable storage medium in a server data processing system and adapted to be downloaded over a network to a remote data processing system for use in a computer readable storage medium within the remote system.

In a representative embodiment, the medicine dispensing application is implemented in a special purpose computer, preferably in software executed by one or more processors. The software is maintained in one or more data stores or memories associated with the one or more processors, and the software may be implemented as one or more computer programs. Collectively, this special-purpose hardware and software comprises the functionality described above.

Further, any authentication or authorization functionality required herein may be implemented as an adjunct or extension to an existing access manager or policy management solution.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

Finally, while given components of the system have been described separately, one of ordinary skill will appreciate that some of the functions may be combined or shared in given instructions, program sequences, code portions, and the like.

The techniques herein provide for improvements to another technology or technical field, namely, identity access and management systems, as well as improvements to the functioning of recertification processes within such systems.

Having described our invention, what we now claim is as follows:

The invention claimed is:

1. A computer-implemented method for registering intelligent containers to a medicine dispensing system, comprising:
   by a medicine dispensing system server, comprising a processor and a memory, receiving a set of events from an intelligent container of a plurality of intelligent containers, wherein each intelligent container comprises a sleeve adapted for receiving a standard medicine bottle, a wireless device, a set of sensors for detecting the set of events including a sensor for detecting a current inserting of a medicine bottle in the sleeve and a sensor for detecting movement of the intelligent container;
   by the medicine dispensing system server, responsive to receiving a first event of the set of events indicating the current inserting of the medicine bottle in the sleeve of a respective intelligent container, initiating and completing a registration process for the respective intelligent container for a medicine in the medicine bottle to the medicine dispensing system server, wherein the respective intelligent container is first associated with the inserted medicine as part of the registration process;
   by the medicine dispensing system server, receiving a request to subscribe to events associated with the inserted medicine in the respective intelligent container from a subscribing device;
   by the medicine dispensing system server, after the registration process determining whether other events of the set of events satisfy a rule associated with the inserted medicine or the intelligent container; and
   by the medicine dispensing system server, sending a message to the subscribing device as a result of the determining.

2. The method as recited in claim 1, further comprising:
   receiving by the intelligent container, an identification event from a proximate wireless device, wherein the identification event can be used to identify the proximate wireless device; and
   sending by the intelligent container the received identification event from the proximate wireless device together with a second event sensed by a sensor in the intelligent container, the second event in the set of events received by the medicine dispensing system server and indicating a physical manipulation of the intelligent container by a user.

3. The method as recited in claim 1, further comprising receiving a request to subscribe to events which satisfy an indication of unauthorized medicine dispensing from the intelligent container.

4. The method as recited in claim 1, wherein the subscribing device presents a graphical interface for presenting events, the graphical interface including a first region for displaying an icon representing a current state of the intelligent container, wherein the state of the intelligent container is any of an upright cap on state, a cap off state and a tilted state.

5. The method as recited in claim 1, wherein respective subsets of events in the set of events are respectively classified as dispensing events, movement events and replacing events and the rule is comprised of events from different of the subsets.

6. The method as recited in claim 2, wherein the identification event includes an IMEI of the proximate wireless device.

7. The method as recited in claim 1, wherein a first intelligent container is associated with a plurality of patients.

8. The method as recited in claim 3, wherein the unauthorized dispensing is based on a cap off event and a tilt event at an unscheduled time.

9. The method as recited in claim 1, further comprising subscribing to events of a subset of intelligent containers containing a certain class of medicines.

10. The method as recited in claim 1, further comprising subscribing to all intelligent containers registered to a first patient.

11. The method as recited in claim 1, further comprising:
receiving an event from a respective intelligent container;
logging an event with the medicine dispensing system server; and
after logging the event with the medicine dispensing system server, sending the event to all subscribers of the event;
wherein all subscribers of the event include subscribers subscribed to events from the respective intelligent container, subscribers subscribed to events about a medicine where the medicine is registered to a plurality of intelligent containers including the respective intelligent container and subscribers subscribed to events from all intelligent containers registered to a respective patient where the respective intelligent container is registered to the respective patient.

12. The method as recited in claim 1, further comprising receiving a selection of a type of notification from a subscriber to send the message, wherein selections available to the subscriber include a first selection of an SMS alert to be immediately sent to the subscribing device or a second selection of a recent history of events to an app on the subscribing device.

13. The method as recited in claim 1, wherein the registration process includes reading encoded information in a bar code or QR code on the medicine by a proximate wireless device.

14. A computer program product in a non-transitory computer readable medium for use in a medicine dispensing system server, the computer program product holding computer program instructions which, when executed by the medicine dispensing system server for registering intelligent containers to a medicine dispensing system server, the computer program instructions comprising:
program code operative to operative to receive a set of events transmitted by an intelligent container of a plurality of intelligent containers, wherein each intelligent container comprises a sleeve adapted for receiving a standard medicine bottle, a wireless device, a set of sensors for detecting the set of events including a sensor for detecting a current inserting of a medicine bottle in the sleeve and a sensor for detecting movement of the intelligent container;
program code responsive to receiving an insertion event of the set of events indicating the current inserting of the medicine bottle in the sleeve of a respective intelligent container for initiating and completing a registration process for the respective intelligent container for a medicine in the medicine bottle with a medicine dispensing system server, wherein the respective intelligent container is first associated with the inserted medicine by the registration process;
program code operative to associate the intelligent container with the inserted medicine and a rule set;
program code operative to receive a request to subscribe to events associated with the medicine or the respective intelligent container from a subscribing device;
program code operative to determine after the registration process whether other events of the set of events satisfy a rule in the rule set; and
program code operative to send a message to the subscribing device as a result of the determining.

15. The computer program product as recited in claim 14, further comprising:
program code operative to receive an identification event from a wireless device proximate to the intelligent container, wherein the identification event can be used to identify the proximate wireless device; and
program code operative to send the received identification event by the intelligent container to the medicine dispensing server system, wherein the received event from the proximate wireless device is sent together with a second event sensed by a sensor in the intelligent container, the second event in the set of events received by the medicine dispensing system server and indicating a physical manipulation of the intelligent container by a user.

16. The computer program product as recited in claim 15, further comprising:
program code operative to associate a container profile with the intelligent container in the medicine dispensing service, wherein the container profile includes a medicine and a schedule for taking the medicine;
program code operative to associate a user profile with the intelligent container, the user profile associated with a user taking the medicine; and
program code operative to subscribe to events associated with a user profile.

17. The computer program product as recited in claim 15 further comprising program code operative to subscribe to events indicating an unauthorized dispensing of a medicine from an intelligent container.

18. The computer program product as recited in claim 14 further comprising program code operative to present a graphical interface on a display, wherein the graphical user interface includes a first region for displaying an icon representing a current state of the intelligent container, wherein the state of the intelligent container is any of an upright cap on state, a cap off state and a tilted state.

19. The computer program product as recited in claim 14 further comprising program code operative to present messages concerning the set of events in a first area of a graphical user interface and the set of events in a second area of the graphical user interface.

20. The computer program product as recited in claim 14 further comprising program code operative to log the set of events.

* * * * *